United States Patent [19]

Khoe

[11] 4,064,253

[45] Dec. 20, 1977

[54] METHOD OF SUPPRESSING SNORING

[76] Inventor: Teng Hian Khoe, Thomsonlaan 80A, Hague, Netherlands

[21] Appl. No.: 729,676

[22] Filed: Oct. 5, 1976

Related U.S. Application Data

[63] Continuation of Ser. No. 638,054, Dec. 5, 1975, abandoned, which is a continuation of Ser. No. 512,610, Oct. 7, 1974, abandoned.

[30] Foreign Application Priority Data

Oct. 10, 1973 Netherlands ......................... 7313964

[51] Int. Cl.$^2$ .......................................... A61K 31/455
[52] U.S. Cl. .................................................... 424/266
[58] Field of Search ............................... 424/266, 195; 260/293.52

[56] References Cited

PUBLICATIONS

The Merck Index, 8th Edition (1968), Published by Merck & Co. Inc. Rahway, N. J., p. 99.

*Primary Examiner*—Donald B. Moyer
*Attorney, Agent, or Firm*—Holman & Stern

[57] ABSTRACT

An anti-snoring composition comprising an arecoline salt, the concentration of said salt being sufficient in order to apply 0.01 to 25 mg of the salt to the cells of the palate in at most 5 minutes.

4 Claims, No Drawings

METHOD OF SUPPRESSING SNORING

This is a continuation of application Ser. No. 638,054 filed on Dec. 5, 1975 now abandoned which in turn is a continuation of application Ser. No. 512,610, filed Oct. 7, 1974, now abandoned.

BACKGROUND OF THE INVENTION

The invention relates to an anti-snore composition and to a method for preparing an anti-snore medicine as well as a method of relieveing snoring by means of this composition.

The tendency or habit of snoring which is exhibited by many people and animals is a source of annoyance for persons in their surrounding and gives rise to sleeplessness, which may cause nervous strains.

It is supposed that the snoring is caused by the suction of air along the soft, hind part of the palate, causing vibrations and an annoying noise.

It has already been attempted to provide an efficient medicine capable of limiting or stopping the snoring or preventing it, but so far these attempts have not been successful.

SUMMARY OF THE INVENTION

The invention aims to satisfy this condition and to provide an efficient anti-snore composition by which means snoring is limited or even entirely suppressed.

It has now been found that particular alkaloid compounds when they are brought into contact with the soft palate are capable of preventing snoring.

According to the invention an anti-snore composition comprises a compound having the general formula

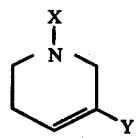

in which X represents an alkyl group, thioalkylgroup, alkoxy group, whether branched or not, containing 1-6 carbon atoms, an amino group, a mono- or dialkyl substituted amino group, or a trimethyl ammonium group, and where Y represents a COO-alkyl or

alkyl group or a pharmaceutically compatible salt in a form which allows the sufficient absorption by the cells of the palate.

The form in which the medicine is administered should be adapted to local applications. So e.g. tablets can be utilized particularly sucking tablets, soluble tablets, dusting powders, sprays, pencils, preparations on a resin base with delayed effect, infusion liquid and peferably gargles.

The effective component incorporated into a composition according to the invention can be represented by the general formula,

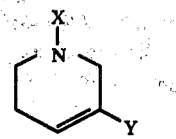

wherein X and Y have the aforementioned signification, but preferably the compound with the formula is used in which X represents a methyl group and Y the group COOCH$_3$, that is to say methyl-N-methyl-1,2,5,6 tetrahydronicotinate also known as arecoline and the pharmaceutically compatible salts thereof derived from inorganic and organic acids. As examples the salt of hydrobromic acid, salt of fumaric acid, tartrate, succinate, valerate, citrate, etc. can be mentioned. Also complex compounds of arecoline whether with a delayed effect or not, or an isomer of arecoline (arecolidine) can be used, but preferably arecoline itself in the shape of salt of hydrobromine is used.

Arecoline in the way known per se can be extracted from ground betel-nuts in which arecoline constitutes the principal alkaloid. The other compounds according to the stated formula may be prepared by starting from arecoline or in an other way known per se.

It has been found in experiments that for an efficient effect of the anti-snore composition according to the invention it is required to bring for a short time a particular quantity of the effective component into contact with the soft palate. For that purpose a concentration such as that of the effective component is incorporated into the composition that, in a period of at most 5 minutes a quantity ranging from 0.01 to 25 mg of effective component may be applied to the cells of the palate.

DESCRIPTION OF PREFERRED EMBODIMENTS

Example I

An anti-snore composition in the form of a gargle is prepared by dissolving 100 mg methyl-N-methyl.1,2,5,6 tetrahydronicotinate-HBr while stirring. If desired flavouring substances may be added in suitable quantities.

The gargle obtained in this way for local oral administration can be used in a dose of from 1 to 2 times, 15 cc at a time, or from 1 to 2 table spoons containing 1.5 to 2 mg close to or immediately before retiring for the night.

If desired the treatment can be performed two times in succession.

Example II

An anti-snore composition to be administered per os in the form of chocolate tablets is prepared by mixing 400 g of molten cocoa butter and cera alba flava as required with 20 g cocoa powder, whereupon to this mixture a quantity of arecoline-HBr ranging from 15 to 200 g is added. From this mixture 100 chocolate tablets are made which per tablet contain from 0.15 to 2 g of the effective component. For treatment one tablet is sucked close to going to bed.

Example III

The manufacture of soluble tablets to be administered per os. A quantity of from 1 to 2 g arecoline-HBr is added to 125 g of milk sugar and to this mixture is admixed 25 g of a tablet making agent. From the mixture obtained 1000 tablets are made with a quantity of of from 1 to 2 mg of effective component per tablet. For each administration 1 to 2 tablets are used which are previously dissolved in a table spoon of water (± 15 ml) with which one gargles for 2 minutes directly before going to bed.

Example IV

Sucking tablets to be administered per os are prepared by mixing a quantity of arecoline-HBr ranging from 7.3 to 146 mg with 40 g of powdered sugar, 25 g of calcium stearate and 8 g of starch. From the mixture, 50 tablets of 1 g each are manufactured. For administration 1 to 2 tablets containing from 0.1 to 2 g of effective component per tablet are used which are sucked in the mouth directly before going to bed.

What I claim is:

1. A method for suppressing snoring in a human host in need thereof comprising orally administering to the palate of said host a snore-suppressively effective amount of arecoline or a pharmaceutically acceptable salt thereof.

2. The method according to claim 1, wherein said arecoline or salt thereof is administered in the form of a gargle.

3. The method according to claim 1, wherein said arecoline or salt thereof is administered in the form of a sucking tablet.

4. The method according to claim 1, wherein said arecoline or salt thereof is administered in a dose of from 0.01 to 25 mg.

* * * * *